(12) United States Patent
Iwakuni et al.

(10) Patent No.: US 11,638,681 B2
(45) Date of Patent: *May 2, 2023

(54) WHITE PIGMENT FOR COSMETICS, AND COSMETIC

(71) Applicant: FUJIMI INCORPORATED, Kiyosu (JP)

(72) Inventors: Mayumi Iwakuni, Kiyosu (JP); Keiji Ashitaka, Kiyosu (JP); Naoya Miwa, Kiyosu (JP)

(73) Assignee: FUJIMI INCORPORATED, Kiyosu (JP)

( * ) Notice: Subject to any disclaimer, the term of this patent is extended or adjusted under 35 U.S.C. 154(b) by 0 days.

This patent is subject to a terminal disclaimer.

(21) Appl. No.: 17/276,288

(22) PCT Filed: Mar. 28, 2019

(86) PCT No.: PCT/JP2019/013799
§ 371 (c)(1),
(2) Date: Mar. 15, 2021

(87) PCT Pub. No.: WO2020/059190
PCT Pub. Date: Mar. 26, 2020

(65) Prior Publication Data
US 2022/0023170 A1    Jan. 27, 2022

(30) Foreign Application Priority Data
Sep. 20, 2018   (JP) ............................. JP2018-176255

(51) Int. Cl.
*A61K 8/29* (2006.01)
*A61K 8/02* (2006.01)
*A61Q 1/12* (2006.01)

(52) U.S. Cl.
CPC .............. *A61K 8/29* (2013.01); *A61K 8/0254* (2013.01); *A61Q 1/12* (2013.01); *A61K 2800/412* (2013.01); *A61K 2800/413* (2013.01); *A61K 2800/43* (2013.01)

(58) Field of Classification Search
None
See application file for complete search history.

(56) References Cited

U.S. PATENT DOCUMENTS

| | | | |
|---|---|---|---|
| 3,556,720 | A | 1/1971 | Cox et al. |
| 3,558,273 | A | 1/1971 | Beck |
| 3,914,381 | A | 10/1975 | Sugahara et al. |
| 2008/0159940 | A1 | 7/2008 | Aupaix et al. |
| 2013/0209387 | A1 | 8/2013 | Pappas et al. |
| 2013/0224140 | A1 | 8/2013 | Pappas et al. |
| 2014/0044971 | A1 | 2/2014 | Sueda |
| 2014/0050925 | A1 | 2/2014 | Sueda |
| 2014/0058029 | A1 | 2/2014 | Sueda |
| 2014/0112862 | A1 | 4/2014 | Sueda |
| 2015/0328097 | A1 | 11/2015 | Pappas et al. |
| 2017/0008773 | A1 | 1/2017 | Pappas et al. |
| 2020/0377369 | A1 | 12/2020 | Iwakuni |
| 2021/0145712 | A1 | 5/2021 | Iwakuni et al. |

FOREIGN PATENT DOCUMENTS

| | | | |
|---|---|---|---|
| CN | 101033062 | A | 9/2007 |
| CN | 102641214 | A * | 8/2012 |
| EP | 3 604 218 | A1 | 2/2020 |
| EP | 3 777 819 | A1 | 2/2021 |
| GB | 1282594 | A | 7/1972 |
| JP | S49-001720 | B1 | 1/1974 |
| JP | S49-019520 | B1 | 5/1974 |
| JP | H10-046135 | A | 2/1998 |
| JP | H10-167929 | A | 6/1998 |
| JP | 2005-505669 | A | 2/2005 |
| JP | 2005-089214 | A | 4/2005 |
| JP | 2007-291090 | A | 11/2007 |
| JP | 2008-503436 | A | 2/2008 |
| JP | 2008-056535 | A | 3/2008 |
| JP | 4649102 | B2 | 3/2011 |
| JP | 4684970 | B1 | 5/2011 |
| JP | 2013-095888 | A | 5/2013 |
| WO | WO-2012/061280 | A2 | 5/2012 |
| WO | WO-2012/147888 | A1 | 11/2012 |
| WO | WO-2018/180797 | A1 | 10/2018 |
| WO | WO-2019/189665 | A1 | 10/2019 |
| WO | WO-2020/059190 | A1 | 3/2020 |
| WO | WO-2020/059191 | A1 | 3/2020 |

OTHER PUBLICATIONS

Onoda et al., "Influence of Temperature and Ultrasonic Treatment on Preparation of Titanium Phosphates and Their Powder Properties", Cosmetics, 1, 2014, pp. 222-231. (Year: 2014).*
Onoda, et al., "Influence of concentration in phosphoric acid treatment of titanium oxide and their powder properties", Journal of Asian Ceramic Societies, vol. 3, No. 1, 2015, pp. 27-31.
Extended European Search Report issued in corresponding European Application No. 19862336.5 dated Oct. 15, 2021.
Extended European Search Report issued in corresponding European Application No. 19862261.5 dated Oct. 13, 2021.
Onoda, et al., "Preparation of titanium phosphates with additives in hydrothermal process and their powder properties for cosmetics", International Journal of Cosmetic Science, 2013, 35, pp. 196-200.
U.S. Appl. No. 17/276,299, filed Mar. 15, 2021, Iwakuni et al.
English translation of the International Preliminary Report on Patentability issued in corresponding application No. PCT/JP2018/011098 dated Oct. 10, 2019.
Extended European Search Report issued in corresponding European Patent Application No. 19777809.5 dated May 7, 2021.
Extended European Search Report issued in European Patent Application No. 21214767.2 dated Mar. 23, 2022.

(Continued)

*Primary Examiner* — Melissa L Fisher
(74) *Attorney, Agent, or Firm* — Foley & Lardner LLP

(57) ABSTRACT

Provided is a white pigment for cosmetics capable of giving a cosmetic that gives a coating film having less stickiness and higher long-lasting properties. A white pigment for cosmetics of the present invention includes a titanium phosphate powder, the titanium phosphate powder includes crystal particles of titanium phosphate, and a ratio (oil absorption value/specific surface area) of an oil absorption value (ml/100 g) to a specific surface area ($m^2$/g) of the crystal particles is 2.0 or more.

5 Claims, 2 Drawing Sheets

(56) References Cited

OTHER PUBLICATIONS

Guo et al., "Synthesis of shape-controlled mesoporous titanium phosphate nanocrystals: The hexagonal titanium phosphate with enhanced hydrogen generation from water splitting", International Journal of Hydrogen , Energy, Elsevier Science Publishers B.V., Barking, GB, vol. 39, No. 6, Dec. 25, 2013 (Dec. 25, 2013), XP028828982, pp. 2446-2453.
Non-Final Office Action on U.S. Appl. No. 16/498,140 dated Aug. 20, 2021.
Non-Final Office Action on U.S. Appl. No. 16/498,140 dated Dec. 7, 2020.
Non-Final Office Action on U.S. Appl. No. 17/043,166 dated May 24, 2022.
Non-Final Office Action on U.S. Appl. No. 17/276,299 dated Mar. 31, 2022.
Notice of Allowance on U.S. Appl. No. 16/498,140 dated Feb. 2, 2022.
Onoda et al., "Preparation of titanium phosphate white pigments with titanium sulfate and their powder properties", Journal of Advanced Ceramics, 3(2): 2014, 132-136.
Onoda et al., "Mechanical Treatment On Powder Properties of Titanium Phosphate White Pigments", Phosphorus Research Bulletin, vol. 29, 2014, pp. 006-010.
US Office Action on U.S. Appl. No. 16/498,140 dated Apr. 12, 2021.
US Final Office Action on U.S. Appl. No. 17/043,166 dated Sep. 26, 2022 (9 pages).
US Final Office Action on U.S. Appl. No. 17/276,299 dated Oct. 20, 2022 (13 pages).

\* cited by examiner

WHITE PIGMENT FOR COSMETICS, AND COSMETIC

TECHNICAL FIELD

The present invention relates to a white pigment for cosmetics.

BACKGROUND ART

White pigments for cosmetics are a base pigment that is mixed with other pigments to give a composition of a cosmetic. As a conventional white pigment for cosmetics, titanium(IV) oxide ($TiO_2$, titanium dioxide, hereinafter also simply called "titanium oxide") has been typically used.

PTL 1 discloses a rutile-type titanium oxide particle aggregate formed by aggregating fan-shaped rutile-type titanium oxide particles that have been formed by assembling and/or bonding rod-shaped particles having a side of 0.05 to 0.2 μm and a thickness of 0.02 to 0.1 μm, and the particle aggregate has a particle diameter of 0.1 to 5.0 μm and an average friction coefficient (MIU value) of not less than 0.2 and less than 0.7. The document also discloses that a cosmetic, specifically a makeup cosmetic, containing the rutile-type titanium oxide particle aggregate can be smoothly applied onto the skin, gives no squeaking feeling or grainy feeling to the skin, and can achieve a natural bare skin appearance without white powdery finish due to appropriate coloration and concealing powers.

CITATION LIST

Patent Literature

PTL 1: JP 4684970 B

SUMMARY OF INVENTION

Technical Problem

The white pigment for cosmetics including the rutile-type titanium oxide particle aggregate disclosed in PTL 1, however, has room for improvement in terms of giving a cosmetic that gives a coating film having no stickiness and satisfactory long-lasting properties.

The present invention is intended to provide a white pigment for cosmetics capable of giving a cosmetic that gives a coating film having less stickiness and higher long-lasting properties.

Solution to Problem

To solve the problems, an aspect of the present invention provides a white pigment for cosmetics including a titanium phosphate powder, the titanium phosphate powder includes crystal particles of titanium phosphate, and a ratio (oil absorption value/specific surface area) of an oil absorption value (ml/100 g) to a specific surface area ($m^2/g$) of the crystal particles is 2.0 or more.

Advantageous Effects of Invention

The white pigment for cosmetics in an aspect of the present invention has a ratio (oil absorption value/specific surface area) of an oil absorption value (ml/100 g) to a specific surface area ($m^2/g$) of the crystal particles of 2.0 or more, and thus a cosmetic containing the white pigment should give a coating film having less stickiness and higher long-lasting properties.

DESCRIPTION OF EMBODIMENTS

Figure 1:
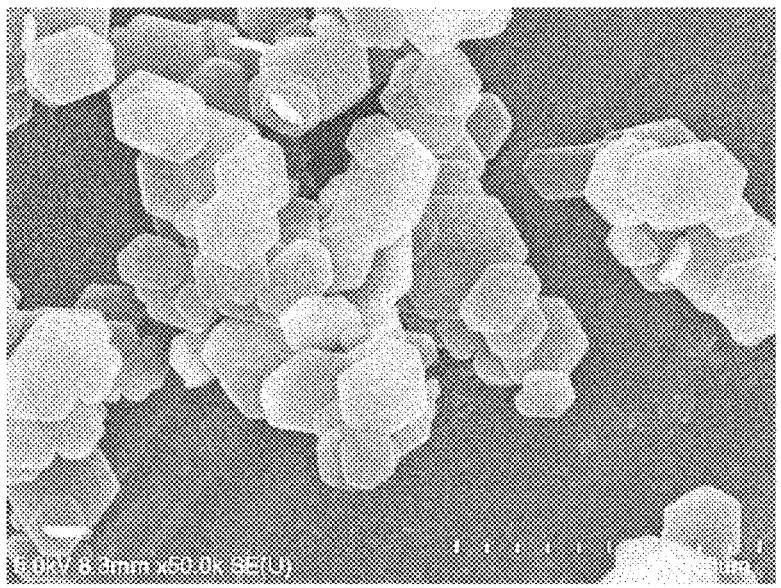
FIG. 1 is a scanning electron micrograph of a powder produced in Example 1.

White pigment for cosmetics according to aspect
As described above, the white pigment for cosmetics according to an aspect of the present invention is a white pigment for cosmetics including a titanium phosphate powder, the titanium phosphate powder includes crystal particles of titanium phosphate, and the ratio (oil absorption value/specific surface area) of an oil absorption value (ml/100 g) to a specific surface area ($m^2/g$) of the crystal particles is 2.0 or more.

The white pigment for cosmetics according to an aspect is, for example, a white pigment including a titanium phosphate powder having a whiteness of 92.91 or more as determined in accordance with JIS Z 8715.

The white pigment for cosmetics according to an aspect is, for example, a white pigment including a titanium phosphate powder having a refractive index of 1.67 or more and 1.83 or less.

The white pigment for cosmetics according to an aspect is, for example, a white pigment for cosmetics including a titanium phosphate powder, the titanium phosphate powder includes crystal particles of titanium phosphate, and the titanium phosphate powder has an average friction coefficient (MIU) of less than 1.45.

The white pigment for cosmetics according to an aspect is, for example, a white pigment in which the crystal particles are plate-like crystal particles.

The white pigment for cosmetics according to an aspect is, for example, a white pigment in which the plate-like crystal particles have an average thickness of 0.01 μm or more and 4 μm or less and an aspect ratio of 5 or more, where the aspect ratio is a value calculated by dividing an average primary particle diameter of the plate-like crystal particles by the average thickness.

The white pigment for cosmetics according to an aspect is, for example, a white pigment in which the titanium phosphate powder has an average primary particle diameter of 0.05 μm or more and 20 μm or less.

A composition including the white pigment for cosmetics according to an aspect may be used as a cosmetic.

Embodiments

Embodiments of the present invention will now be described, but the present invention is not limited to the embodiments described below. The embodiments described below include technically preferred limitations for carrying out the present invention, but the limitations are not essential requirements of the invention.

First Embodiment

A white pigment for cosmetics in a first embodiment includes a titanium phosphate powder. The titanium phosphate powder includes titanium phosphate crystal particles.

The titanium phosphate crystal particles are plate-like crystal particles. The plate-like crystals have an average primary particle diameter (for example, a value calculated from, as particle diameters, diameters determined by an image analysis method in which a plate is converted into a circle) of 0.05 µm or more and 20 µm or less and an average thickness of 0.01 µm or more and 4 µm or less. The plate-like crystals have an aspect ratio (a value calculated by dividing an average primary particle diameter by an average thickness) of 5 or more.

The titanium phosphate powder has a whiteness of 100.51 as determined in accordance with JIS Z 8715.

The titanium phosphate powder has a refractive index of 1.79.

The titanium phosphate powder has an oil absorption value of 116 ml/100 gas determined in accordance with JIS K 5101-13. The titanium phosphate powder has a ratio (oil absorption value/specific surface area) of an oil absorption value (ml/100 g) to a specific surface area ($m^2/g$) of the titanium phosphate crystal particles of 2.0 or more.

The white pigment for cosmetics in the embodiment has a high whiteness of 100.51 and thus can exhibit a high function as a base pigment when mixed with other pigments to give a cosmetic composition.

The white pigment for cosmetics in the embodiment has a refractive index of 1.79, which is moderately higher than the refractive index (1.5) of the human skin, and thus a cosmetic composition containing the white pigment can give a cosmetic achieving a moderate covering function and natural finish without white powdery finish.

The white pigment for cosmetics in the embodiment includes a titanium phosphate powder including crystal particles of titanium phosphate and has a ratio (oil absorption value/specific surface area) of an oil absorption value (ml/100 g) to a specific surface area ($m^2/g$) of the crystal particles of 2.0 or more. Hence, a cosmetic containing the white pigment gives a coating film that has less stickiness and is unlikely to undergo makeup deterioration by sebum.

The white pigment for cosmetics in the embodiment includes a titanium phosphate powder including plate-like crystal particles of titanium phosphate. The titanium phosphate powder has an average primary particle diameter of 0.05 µm or more and 20 µm or less, and the plate-like crystal particles have an average thickness of 0.01 µm or more and 4 µm or less and an aspect ratio of 5 or more. The titanium phosphate powder has an average friction coefficient (MIU) of less than 1.45. Accordingly, a cosmetic containing the white pigment has excellent slidability.

The titanium phosphate powder may be produced by the following method, for example.

First, an aqueous solution of titanium sulfate and an aqueous solution of phosphoric acid are mixed at such a ratio that the phosphorus molarity [P] to the titanium molarity [Ti], [P]/[Ti], is 5 or more and 21 or less, giving a liquid mixture. Next, the liquid mixture is placed in a closed container and is maintained at a temperature of 100° C. or more and 160° C. or less to undergo reaction for a predetermined period (for example, 5 hours or more). In other words, hydrothermal synthesis is performed. The pressure in the closed container is higher than the atmospheric pressure and is naturally determined by a pressing temperature. A slurry containing crystal particles of titanium phosphate is thus prepared.

Next, the prepared slurry is cooled, and then a solid content (crystal particles of titanium phosphate) is separated from the slurry. The resulting solid content is cleaned with a cleaning solution containing aqueous ammonia (ammonium hydroxide) and then is dried.

Second Embodiment

A white pigment for cosmetics in a second embodiment includes a titanium phosphate powder. The titanium phosphate powder includes titanium phosphate crystal particles. The titanium phosphate crystal particles are plate-like crystal particles. The plate-like crystals have an average primary particle diameter (for example, a value calculated from, as particle diameters, diameters determined by an image analysis method in which a plate is converted into a circle) of 0.05 µm or more and 20 µm or less and an average thickness of 0.01 µm or more and 4 µm or less. The plate-like crystals have an aspect ratio (a value calculated by dividing an average primary particle diameter by an average thickness) of 5 or more.

The titanium phosphate powder has a whiteness of 96.32 to 97.47 as determined in accordance with JIS Z 8715.

The titanium phosphate powder has a refractive index of 1.73 to 1.83.

The titanium phosphate powder has an oil absorption value of 45 ml/100 g or more and 77 ml/100 g or less as determined in accordance with JIS K 5101-13. The titanium phosphate powder has a ratio (oil absorption value/specific surface area) of an oil absorption value (ml/100 g) to a specific surface area ($m^2/g$) of the titanium phosphate crystal particles of 2.0 or more.

The white pigment for cosmetics in the embodiment has a high whiteness of 96.32 to 97.47 and thus can exhibit a high function as a base pigment when mixed with other pigments to give a cosmetic composition.

The white pigment for cosmetics in the embodiment has a refractive index of 1.73 to 1.83, which is moderately higher than the refractive index (1.5) of the human skin, and thus a cosmetic composition containing the white pigment can give a cosmetic achieving a moderate covering function and natural finish without white powdery finish.

The white pigment for cosmetics in the embodiment includes a titanium phosphate powder including crystal particles of titanium phosphate and has a ratio (oil absorption value/specific surface area) of an oil absorption value (ml/100 g) to a specific surface area ($m^2/g$) of the crystal particles of 2.0 or more. Hence, a cosmetic containing the white pigment gives a coating film that has less stickiness and is unlikely to undergo makeup deterioration by sebum.

The white pigment for cosmetics in the embodiment includes a titanium phosphate powder including plate-like crystal particles of titanium phosphate. The titanium phosphate powder has an average primary particle diameter of 0.05 µm or more and 20 µm or less, and the plate-like crystal particles have an average thickness of 0.01 µm or more and 4 µm or less and an aspect ratio of 5 or more. The titanium phosphate powder has an average friction coefficient (MIU) of less than 1.45. Accordingly, a cosmetic containing the white pigment has excellent slidability. In other words, a cosmetic containing the white pigment for cosmetics in the embodiment can be smoothly applied onto the skin.

The titanium phosphate powder may be produced by the following method, for example.

First, an aqueous solution of titanyl sulfate and an aqueous solution of phosphoric acid are mixed at such a ratio that the phosphorus molarity [P] to the titanium molarity [Ti], [P]/[Ti], is 5 or more and 21 or less, giving a liquid mixture. Next, the liquid mixture is placed in a closed container and is maintained at a temperature of 100° C. or more and 160°

C. or less to undergo reaction for a predetermined period (for example, 5 hours or more). In other words, hydrothermal synthesis is performed. The pressure in the closed container is higher than the atmospheric pressure and is naturally determined by a pressing temperature. A slurry containing crystal particles of titanium phosphate is thus prepared.

Next, the prepared slurry is cooled, and then a solid content (crystal particles of titanium phosphate) is separated from the slurry. The resulting solid content is cleaned with water and then is dried.

In the above embodiments, titanium sulfate and titanyl sulfate are used as the titanium source to give crystalline titanium phosphate powders as examples, and other examples of the titanium source include peroxotitanic acid.

The crystalline titanium phosphate powder included in the white pigment for cosmetics preferably includes plate-like crystal particles of titanium phosphate having an average primary particle diameter of 0.10 µm or more and 20 µm or less and an aspect ratio of 5 or more. The average primary particle diameter is more preferably 0.2 µm or more and 10 µm or less, and the aspect ratio is more preferably 9 or more. The ratio (oil absorption value/specific surface area) of an oil absorption value (ml/100 g) to a specific surface area ($m^2$/g) of the crystal particles included in the titanium phosphate powder included in the white pigment for cosmetics is preferably 3.0 or more.

A cosmetic containing a powder having a higher ratio (oil absorption value/specific surface area) gives a coating film that has less stickiness and is unlikely to undergo makeup deterioration by sebum, but a powder having an excessively high ratio unfortunately gives compounds having larger variations in viscosity, bulk density, and the like when a cosmetic is produced. From this viewpoint, the ratio is preferably 200.0 or less.

The average friction coefficient (MIU) is preferably 1.40 or less and more preferably 1.35 or less. A cosmetic containing a powder having a smaller average friction coefficient (MIU) can be more smoothly applied onto the skin, but a cosmetic containing a powder having an excessively small average friction coefficient has poor adhesion to the skin. From this viewpoint, the average friction coefficient is preferably 0.20 or more and more preferably 0.65 or more.

Cosmetic

Examples of the cosmetic including a composition containing a white pigment powder (hereinafter called "cosmetic composition") include makeup cosmetics such as a foundation, a face powder, a cheek rouge, and an eye shadow; and skin care cosmetics such as a whitening powder and a body powder. The white pigments in the first embodiment and the second embodiment are suitable for the white pigment in these cosmetic compositions.

When the white pigment is used as an additive in a foundation or the like, which is intended to have a covering function, brightness, or the like, a titanium phosphate powder having an average primary particle diameter of 1 µm or more and 20 µm or less is preferably used.

EXAMPLES

Example 1

First, an aqueous solution of titanium sulfate and an aqueous solution of phosphoric acid were mixed at such a ratio that the phosphorus molarity [P] to the titanium molarity [Ti], [P]/[Ti], was 13, giving a liquid mixture. Next, the liquid mixture was placed in a closed container (an internal volume of 100 mL) and was maintained at a temperature of 110° C. to undergo reaction for 5 hours.

After the reaction, the lid was removed, a slurry in the container was cooled to room temperature and then was taken out of the container, and a solid content was separated from the slurry by filtration. The solid content was cleaned with 29% aqueous ammonia (an aqueous solution of an ammonium salt) and then was dried (by standing at a temperature of 105° C. for 24 hours), giving a powder.

The resulting powder was analyzed by using an X-ray diffractometer, and the result revealed that the particles included in the powder were a crystalline titanium phosphate having a structural formula of $Ti(HPO_4)_2 \cdot H_2O$.

The whiteness of the resulting powder was determined by using an ultraviolet and visible spectrophotometer "UV-2450" manufactured by Shimadzu Corporation with an illuminant D65 in a condition of a visual field of 2° to be 100.51. In other words, the resulting powder had a whiteness of 100.51 as determined in accordance with JIS Z 8715.

The resulting powder was observed under a scanning electron microscope, and the result revealed that, as illustrated in FIG. 1, the particles included in the powder had a plate-like shape, and many hexagonal plates were included. From an image under the scanning electron microscope, the average thickness of the crystal particles included in the resulting powder was determined to be 0.017 µm. An image under the scanning electron microscope was analyzed by using an image analysis software "Mac-View ver. 4" manufactured by Mountech Co. Ltd., and the average primary particle diameter of the crystal particles included in the resulting powder was determined to be 0.24 µm. Calculation was performed by using these measured values (0.24/0.017), and the aspect ratio of the crystal particles included in the resulting powder was determined to be 14.

The refractive index of the resulting powder was determined by the following method to be 1.79.

First, the resulting powder and polymethyl methacrylate (film substrate: a transparent resin to be a film base) were added to and mixed with N-methylpyrrolidone (a solvent capable of dissolving the film substrate) to give a liquid in which the powder was dispersed and polymethyl methacrylate was dissolved. The content of the powder was changed to give a plurality of liquids. Each liquid was used to forma coated film having a thickness of 600 µm on a PET film, and then the coated film was dried at 80° C. to give a film including only the powder and the resin. After cooling, the film was released from the PET film.

Each refractive index of a plurality of the films prepared as above was determined by using a refractometer "Prism Coupler, model 2010/M" manufactured by Metricon with a helium-neon laser beam having a wavelength of 632.8 nm as a light source. The measured values of the refractive indexes of the plurality of films were plotted on a graph with the horizontal axis representing powder content (% by volume) and the vertical axis representing refractive index, and the plots were approximated by a straight line. The straight line was extrapolated to a point at which the powder content was 100%, and the refractive index at the point was regarded as the refractive index of the powder.

The oil absorption value of 100 g of the resulting powder was determined by a method in accordance with JIS K 5101-13 to be 116 ml/100 g. The specific surface area of the resulting powder was determined by using a fully automatic specific surface area analyzer "Macsorb (registered trademark) HM-1210" manufactured by Mountech Co. Ltd. by BET fluid process to be 25.0 $m^2$/g. Calculation was performed by using these measured values (116/25.0), and the ratio (oil absorption value/specific surface area) of an oil absorption value (ml/100 g) to a specific surface area ($m^2$/g) of the crystal particles included in the resulting powder was determined to be 4.6.

The average friction coefficient (MIU) of the resulting powder was determined by using a friction tester "KES-SE" manufactured by Kato Tech to be 1.37. The measurement was performed by using a 10-mm square silicon sensor in conditions of a static load of 25 g and a scan speed of 1 mm/sec.

The resulting powder had a bulk density of 0.13 g/ml and a specific gravity of 2.59. The resulting powder had no photocatalytic activity.

A cosmetic composition containing the resulting powder as a white pigment was prepared. The resulting powder had a high whiteness (100.51) and thus was able to exhibit a high function as the base pigment. In addition, the resulting powder had a moderately higher refractive index (1.79) than the refractive index (1.5) of the human skin, and thus use of the prepared cosmetic composition achieved a moderate covering function and natural finish without white powdery finish. Moreover, the resulting powder had an "oil absorption value/specific surface area" of 4.6 (in the range not less than 2.0), and thus the prepared cosmetic composition gave a coating film having less stickiness and lasting long. The resulting powder had a plate-like crystal shape (an aspect ratio of 14) and had an average friction coefficient (MIU) of 1.37, and thus the prepared cosmetic composition also had excellent slidability. In other words, the cosmetic containing the powder was able to be smoothly applied onto the skin.

Example 2

First, an aqueous solution of titanyl sulfate and an aqueous solution of phosphoric acid were mixed at such a ratio that the phosphorus molarity [P] to the titanium molarity [Ti], [P]/[Ti], was 13, giving a liquid mixture. Next, the liquid mixture was placed in a closed container (an internal volume of 100 mL) and was maintained at a temperature of 110° C. to undergo reaction for 5 hours.

After the reaction, the lid was removed, a slurry in the container was cooled to room temperature and then was taken out of the container, and a solid content was separated from the slurry by filtration. The solid content was cleaned with water and then was dried (by standing at a temperature of 105° C. for 24 hours), giving a powder.

The resulting powder was analyzed by using an X-ray diffractometer, and the result revealed that the particles included in the powder were a crystalline titanium phosphate having a structural formula of $Ti(HPO_4)_2 \cdot H_2O$.

The whiteness of the resulting powder was determined by using an ultraviolet and visible spectrophotometer "UV-2450" manufactured by Shimadzu Corporation with an illuminant D65 in a condition of a visual field of 2° to be 97.47. In other words, the resulting powder had a whiteness of 97.47 as determined in accordance with JIS Z 8715.

The resulting powder was observed under a scanning electron microscope, and the result revealed that, as with Example 1, the particles included in the powder had a plate-like shape, and many hexagonal plates were included. From an image under the scanning electron microscope, the average thickness of the crystal particles included in the resulting powder was determined to be 0.026 μm. An image under the scanning electron microscope was analyzed by using an image analysis software "Mac-View ver. 4" manufactured by Mountech Co. Ltd., and the average primary particle diameter of the crystal particles included in the resulting powder was determined to be 0.30 μm. Calculation was performed by using these measured values (0.30/0.026), and the aspect ratio of the crystal particles included in the resulting powder was determined to be 12.

The refractive index of the resulting powder was determined by the same method as in Example 1 to be 1.83. In other words, the resulting powder had a refractive index of 1.83 as determined in accordance with JIS K 7142.

The oil absorption value of 100 g of the resulting powder was determined by a method in accordance with JIS K 5101-13 to be 77 ml/100 g. The specific surface area of the resulting powder was determined by using a fully automatic specific surface area analyzer "Macsorb (registered trademark) HM-1210" manufactured by Mountech Co. Ltd. by BET fluid process to be 22.7 $m^2$/g. Calculation was performed by using these measured values (77/22.7), and the ratio (oil absorption value/specific surface area) of an oil absorption value (ml/100 g) to a specific surface area ($m^2$/g) of the crystal particles included in the resulting powder was determined to be 3.4.

The resulting powder had a bulk density of 0.13 g/ml and a specific gravity of 2.59. The resulting powder had no photocatalytic activity.

A cosmetic composition containing the resulting powder as a white pigment was prepared. The resulting powder had a high whiteness (97.47) and thus was able to exhibit a high function as the base pigment. In addition, the resulting powder had a moderately higher refractive index (1.83) than the refractive index (1.5) of the human skin, and thus use of the prepared cosmetic composition achieved a moderate covering function and natural finish without white powdery finish. Moreover, the resulting powder had an "oil absorption value/specific surface area" of 3.4 (in the range not less than 2.0), and thus the prepared cosmetic composition gave a coating film having less stickiness and lasting long. The resulting powder had a plate-like crystal shape (an aspect ratio of 12), and thus the prepared cosmetic composition also had excellent slidability.

Example 3

First, an aqueous solution of titanyl sulfate and an aqueous solution of phosphoric acid were mixed at such a ratio that the phosphorus molarity [P] to the titanium molarity [Ti], [P]/[Ti], was 11, giving a liquid mixture. Next, the liquid mixture was placed in a closed container (an internal volume of 100 mL) and was maintained at a temperature of 130° C. to undergo reaction for 5 hours.

After the reaction, the lid was removed, a slurry in the container was cooled to room temperature and then was taken out of the container, and a solid content was separated from the slurry by filtration. The solid content was cleaned with water and then was dried (by standing at a temperature of 105° C. for 24 hours), giving a powder.

The resulting powder was analyzed by using an X-ray diffractometer, and the result revealed that the particles included in the powder were a crystalline titanium phosphate having a structural formula of $Ti(HPO_4)_2 \cdot H_2O$.

The whiteness of the resulting powder was determined by using an ultraviolet and visible spectrophotometer "UV-2450" manufactured by Shimadzu Corporation with an illuminant D65 in a condition of a visual field of 2° to be 96.32. In other words, the resulting powder had a whiteness of 96.32 as determined in accordance with JIS Z 8715.

Figure 2:
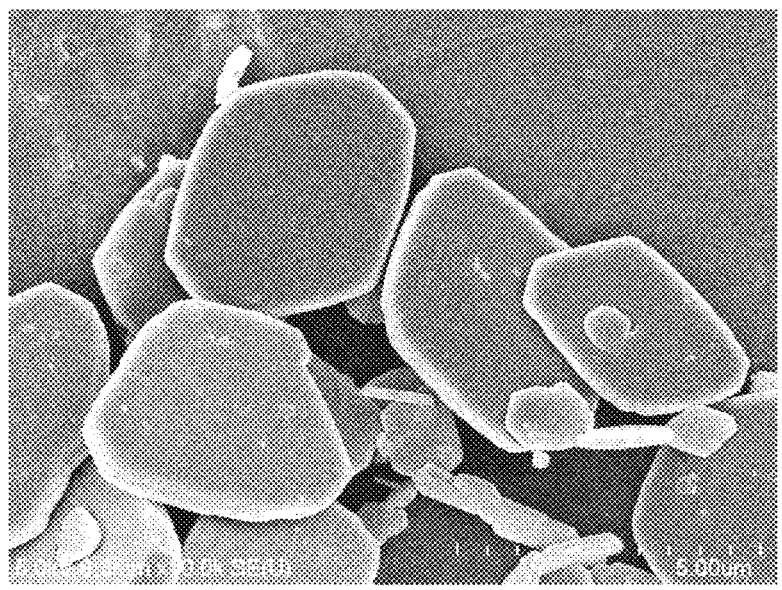
FIG. 2 is a scanning electron micrograph of a powder produced in Example 3.

The resulting powder was observed under a scanning electron microscope, and the result revealed that, as illustrated in FIG. 2, the particles included in the powder had a plate-like shape, and many hexagonal plates were included. From an image under the scanning electron microscope, the average thickness of the crystal particles included in the resulting powder was determined to be 0.27 μm. An image under the scanning electron microscope was analyzed by using an image analysis software "Mac-View ver. 4" manufactured by Mountech Co. Ltd., and the average primary particle diameter of the crystal particles included in the resulting powder was determined to be 3.04 μm. Calculation was performed by using these measured values (3.04/0.27), and the aspect ratio of the crystal particles included in the resulting powder was determined to be 11.

The refractive index of the resulting powder was determined by the same method as in Example 1 to be 1.73.

The oil absorption value of 100 g of the resulting powder was determined by a method in accordance with JIS K 5101-13 to be 45 ml/100 g. The specific surface area of the resulting powder was determined by using a fully automatic specific surface area analyzer "Macsorb (registered trademark) HM-1210" manufactured by Mountech Co. Ltd. by BET fluid process to be 1.65 $m^2/g$. Calculation was performed by using these measured values (45/1.65), and the ratio (oil absorption value/specific surface area) of an oil absorption value (ml/100 g) to a specific surface area ($m^2/g$) of the crystal particles included in the resulting powder was determined to be 27.3.

The average friction coefficient (MIU) of the resulting powder was determined by using a friction tester "KES-SE" manufactured by Kato Tech to be 0.99. The measurement was performed by using a 10-mm square silicon sensor in conditions of a static load of 25 g and a scan speed of 1 mm/sec.

The resulting powder had a bulk density of 0.33 g/ml and a specific gravity of 2.59. The resulting powder had no photocatalytic activity.

A cosmetic composition containing the resulting powder as a white pigment was prepared. The resulting powder had a high whiteness (96.32) and thus was able to exhibit a high function as the base pigment. In addition, the resulting powder had a moderately higher refractive index (1.73) than the refractive index (1.5) of the human skin, and thus use of the prepared cosmetic composition achieved a moderate covering function and natural finish without white powdery finish. Moreover, the resulting powder had an "oil absorption value/specific surface area" of 27.3 (in the range not less than 2.0), and thus the prepared cosmetic composition gave a coating film having less stickiness and lasting long.

The resulting powder had a plate-like crystal shape (an aspect ratio of 11) and had an average friction coefficient (MIU) of 0.99, and thus the prepared cosmetic composition also had excellent slidability. In other words, the cosmetic containing the powder was able to be smoothly applied onto the skin.

Comparative Example 1

First, an aqueous solution of titanium sulfate and an aqueous solution of phosphoric acid were placed in an open vessel at such a ratio that the phosphorus molarity [P] to the titanium molarity [Ti], [P]/[Ti], was 1.3, and the whole was stirred without heat. As a result, an amorphous gel was formed, and the open vessel contained a mixture of the gel and water.

Next, the mixture was cleaned with water and was filtered to collect the gel. The gel was dried (by standing at a temperature of 105° C. for 24 hours), and the dried product was crushed by using a jet mill, giving a powder.

The resulting powder was analyzed by using an X-ray diffractometer and a fluorescent X-ray analyzer, and the result revealed that the particles included in the powder were an amorphous titanium phosphate having a structural formula of $Ti_3(HPO_4)_4$.

The whiteness of the resulting powder was determined by using an ultraviolet and visible spectrophotometer "UV-2450" manufactured by Shimadzu Corporation with an illuminant D65 in a condition of a visual field of 2° to be 92.91. In other words, the resulting powder had a whiteness of 92.91 as determined in accordance with JIS Z 8715.

The resulting powder was observed under a scanning electron microscope. An image under the scanning electron microscope was analyzed by using an image analysis software "Mac-View ver. 4" manufactured by Mountech Co. Ltd., and the average primary particle diameter of the resulting powder was determined to be 0.05 μm.

The refractive index of the resulting powder was determined by the same method as in Example 1 to be 1.67.

The oil absorption value of 100 g of the resulting powder was determined by a method in accordance with JIS K 5101-13 to be 72 ml/100 g. The specific surface area of the resulting powder was determined by using a fully automatic specific surface area analyzer "Macsorb (registered trademark) HM-1210" manufactured by Mountech Co. Ltd. by BET fluid process to be 62.6 $m^2/g$. Calculation was performed by using these measured values (72/62.6), and the ratio (oil absorption value/specific surface area) of an oil absorption value (ml/100 g) to a specific surface area ($m^2/g$) of the crystal particles included in the resulting powder was determined to be 1.2.

The resulting powder had no photocatalytic activity.

A cosmetic composition containing the resulting powder as a white pigment was prepared. The resulting powder had a high whiteness and thus was able to exhibit a high function as the base pigment. In addition, the resulting powder had a moderately higher refractive index (1.67) than the refractive index (1.5) of the human skin, and thus use of the prepared cosmetic composition achieved a moderate covering function and natural finish without white powdery finish.

The resulting powder, however, had an "oil absorption value/specific surface area" of 1.2 (out of the range not less than 2.0), and thus the cosmetic composition prepared in Comparative Example 1 gave a coating film having high stickiness and was likely to cause makeup deterioration as compared with the cosmetic compositions prepared in Examples 1 to 3. The resulting powder included amorphous titanium phosphate particles, and thus the cosmetic composition prepared in Comparative Example 1 was inferior in slidability to the cosmetic compositions prepared in Examples 1 to 3.

Comparative Example 2

As a rutile-type titanium oxide powder, particulate titanium oxide "MT-500B" was purchased from Tayca Corporation. The titanium oxide powder had an average primary particle diameter of 35 nm (according to a catalog). The whiteness of the titanium oxide powder was determined by using an ultraviolet and visible spectrophotometer "UV-2450" manufactured by Shimadzu Corporation with an illuminant D65 in a condition of a visual field of 2° to be 92.47. In other words, the titanium oxide powder had a whiteness of 92.47 as determined in accordance with JIS Z 8715.

The refractive index of the titanium oxide powder was determined by the same method as in Example 1 to be 2.6.

The oil absorption value of 100 g of the titanium oxide powder was determined by a method in accordance with JIS K 5101-13 to be 62 ml/100 g. The specific surface area of the resulting powder was determined by using a fully automatic specific surface area analyzer "Macsorb (registered trademark) HM-1210" manufactured by Mountech Co. Ltd. by BET fluid process to be 40.4 m$^2$/g. Calculation was performed by using these measured values (62/40.4), and the ratio (oil absorption value/specific surface area) of an oil absorption value (ml/100 g) to a specific surface area (m$^2$/g) of the crystal particles included in the resulting powder was determined to be 1.5.

The average friction coefficient (MIU) of the resulting powder was determined by using a friction tester "KES-SE" manufactured by Kato Tech to be 1.52. The measurement was performed by using a 10-mm square silicon sensor in conditions of a static load of 25 g and a scan speed of 1 mm/sec.

A cosmetic composition containing the titanium oxide powder as a white pigment was prepared. The titanium oxide powder had a high whiteness and thus was able to exhibit a high function as the base pigment. The titanium oxide powder, however, had an excessively higher refractive index (2.6) than the refractive index (1.5) of the human skin, and thus the prepared cosmetic composition had a covering function but was likely to cause white powdery finish. In addition, the resulting powder had an "oil absorption value/specific surface area" of 1.5 (out of the range not less than 2.0), and thus the prepared cosmetic composition gave a coating film having high stickiness and was likely to cause makeup deterioration by sebum.

The titanium oxide powder had no plate-like crystal shape and had an average friction coefficient (MIU) of 1.52, and thus the cosmetic composition prepared in Comparative Example 2 was inferior in slidability to the cosmetic compositions prepared in Examples 1 to 3.

Physical properties and the like of those in Examples and Comparative Examples are listed in Table 1.

TABLE 1

| | Powder material | Ti material | P material | P/Ti | Synthetic conditions | Cleaning solution | Whiteness | Average thickness (μm) |
|---|---|---|---|---|---|---|---|---|
| Example 1 | Crystalline titanium phosphate | Titanium sulfate | Phosphoric acid | 13 | 110° C., 5 H | Aqueous ammonia | 100.5 | 0.017 |
| Example 2 | Crystalline titanium phosphate | Titanyl sulfate | Phosphoric acid | 13 | 110° C., 5 H | Water | 97.47 | 0.026 |
| Example 3 | Crystalline titanium phosphate | Titanyl sulfate | Phosphoric acid | 11 | 130° C., 5 H | Water | 96.32 | 0.27 |
| Comparative Example 1 | Amorphous titanium phosphate | Titanium sulfate | Phosphoric acid | 1.3 | Ordinary temperature | Water | 92.91 | — |
| Comparative Example 2 | Rutile-type titanium oxide | — | — | — | — | — | 92.47 | — |

| | Average primary particle diameter (μm) | Aspect ratio | Refractive index | Oil absorption value (ml/100 g) | SA (m$^2$/g) | Oil absorption value/SA | MIU |
|---|---|---|---|---|---|---|---|
| Example 1 | 0.24 | 14 | 1.79 | 116 | 25.0 | 4.6 | 1.37 |
| Example 2 | 0.30 | 12 | 1.83 | 77 | 22.7 | 3.4 | — |
| Example 3 | 3.04 | 11 | 1.73 | 45 | 1.65 | 27.3 | 0.99 |
| Comparative Example 1 | 0.05 | — | 1.67 | 72 | 62.6 | 1.2 | — |
| Comparative Example 2 | 0.035 | — | 2.60 | 62 | 40.4 | 1.5 | 1.52 |

The above results reveal that the white pigment for cosmetics including a crystalline titanium phosphate powder having an "oil absorption value/specific surface area" of 2.0 or more is superior in less stickiness and higher long-lasting properties of a coating film of a cosmetic including the white pigment, to the white pigment for cosmetics including an amorphous titanium phosphate powder and the white pigment for cosmetics including a titanium oxide powder each having an "oil absorption value/specific surface area" of less than 2.0.

The invention claimed is:

1. A white pigment for cosmetics, the white pigment comprising:
   a titanium phosphate powder, the titanium phosphate powder including crystal particles of titanium phosphate, wherein the crystal particles are plate-like crystal particles having an average thickness of 0.01 μm or more and 0.026 μm or less;
   wherein a ratio (oil absorption value/specific surface area) of an oil absorption value (ml/100 g) to a specific surface area (m2/g) of the crystal particles is 2.0 or more.

2. The white pigment for cosmetics according to claim 1, wherein
   the plate-like crystal particles have an aspect ratio of 5 or more, where the aspect ratio is a value calculated by dividing an average primary particle diameter of the plate-like crystal particles by the average thickness.

3. The white pigment for cosmetics according to claim 1, wherein the titanium phosphate powder has an average primary particle diameter of 0.05 μm or more and 20 μm or less.

4. A cosmetic comprising:
a composition containing the white pigment for cosmetics according to claim 1.

5. The white pigment for cosmetics according to claim 2, wherein the titanium phosphate powder has an average primary particle diameter of 0.05 μm or more and 20 μm or less.

* * * * *